United States Patent [19]

Moore, Jr.

[11] 4,108,172
[45] Aug. 22, 1978

[54] CARBON DIOXIDE ABSORPTION CANISTER FOR USE WITH ANALGESIA EQUIPMENT

[76] Inventor: George B. Moore, Jr., 23203 56th W., Mountlake Terrace, Wash. 98043

[21] Appl. No.: 806,446

[22] Filed: Jun. 14, 1977

Related U.S. Application Data

[63] Continuation of Ser. No. 616,857, Sep. 25, 1975, abandoned.

[51] Int. Cl.² ............................................. A61M 16/00
[52] U.S. Cl. .................................................... 128/188
[58] Field of Search .............. 128/188, 191 R, 191 A, 128/145.6, 145.7, 145.8, 142 R, 142.2, 195, 186, 194, 205, 202, 211; 23/284, 252; 55/DIG. 33, DIG. 55, 387, 494

[56] References Cited

U.S. PATENT DOCUMENTS

| | | | |
|---|---|---|---|
| 2,586,670 | 2/1952 | Lambertsen | 55/387 |
| 2,586,677 | 2/1952 | Marrett | 128/188 |
| 2,614,561 | 10/1952 | Fox | 128/191 R |
| 2,837,413 | 6/1958 | Hay | 128/191 R X |
| 2,877,098 | 3/1959 | Ruth | 23/284 |
| 3,202,150 | 8/1965 | Miller | 128/142.2 |
| 3,378,005 | 4/1968 | Smith, Jr. | 128/188 |
| 3,589,870 | 6/1971 | Rankin | 23/284 X |
| 3,612,048 | 10/1971 | Takaoka | 128/191 R X |
| 3,615,233 | 10/1971 | Doering | 128/191 R X |
| 3,738,360 | 4/1971 | Dryden | 128/188 |
| 3,830,632 | 8/1974 | Guzay | 128/191 R X |

*Primary Examiner*—Robert W. Michell
*Assistant Examiner*—Henry J. Recla
*Attorney, Agent, or Firm*—Christensen, O'Connor, Johnson & Kindness

[57] ABSTRACT

A carbon dioxide absorption canister is used with a closed circuit or circle analgesia apparatus, including a gas supply machine, a face mask for the patient, and inhalation and exhalation conduits. The carbon dioxide absorption canister is operatively coupled to both the gas supply machine and the face mask. The canister is composed of a container having a cylindrically shaped side wall with an integral bottom and a removable lid. Both the container and the lid are composed of a synthetic, transparent, resinous material such as an acrylic resin. The gas inlet from the patient to the canister is located at the bottom and contains a check valve that allows flow only into the canister through the inlet. An absorption medium support tray, positioned in the container and spaced above the bottom of the container, supports a quantity of absorption medium, such as soda lime. The outlet from the container is located in the lid and contains a second check valve that only allows flow from the container through the outlet. A third fitting on the bottom of the container operatively couples an expansible air bag with the interior of the container.

14 Claims, 7 Drawing Figures

CARBON DIOXIDE ABSORPTION CANISTER FOR USE WITH ANALGESIA EQUIPMENT

This is a continuation, of application Ser. No. 616,857, filed Sept. 25, 1975, and now abandoned the benefit of the filing data of which is hereby claimed under 35 USC 120.

BACKGROUND OF THE INVENTION

The present invention relates to analgesia equipment, and more particularly to an improved carbon dioxide absorption canister for use with a closed circuit or circle analgesia administering apparatus.

The closed circuit or circle technique for administering an anesthetic or an analgesic such as nitrous oxide employs a patient nose mask, having both an inhalation tube or conduit and an exhalation tube coupled to a carbon dioxide absorption canister. An analgesia gas supply machine is also coupled to the inhalation tube. Check valves are normally associated with the inhalation and exhalation tubes to provide a unidirectional, closed fluid flow circuit from the canister through the mask and back to the canister. Oxygen metabolized to carbon dioxide in the patient's system is replaced by gas from the gas supply machine coupled to the inhalation tube along with an analgesic gas. The advantages of the closed circuit or circle administration technique over the open end administration technique are a reduction in the volume of gas flow from the supply machine by one-half to two-thirds of the amount otherwise required, reduction of exposure for the doctor and his assistants to the hazards of continuous inhalation of nitrous oxide or other analgesic gas, and elimination of the nose mask relief valve. Present equipment for administering anesthetics and analgesics using the closed circuit technique is relatively expensive, relatively bulky, and because of its construction, continuous visual monitoring of the operation of the check valves, the pressure relief valve, and the carbon dioxide absorption medium is especially difficult with present equipment.

It is an object of the present invention to provide an improved, relatively inexpensive, reliable, safe, and corrosion-proof absorption canister for use with closed circuit analgesia equipment. Additional objects of the present invention are to provide a carbon dioxide absorption canister of simple construction having a relief valve that can be coupled to an outside exhaust conduit, to provide a canister having a simple, dual function relief and moisture drain valve, to provide a canister having visually monitorable, check valves incorporated into the canister structure, to provide a canister with a means for visually monitoring the effectiveness of the absorption medium within the canister, to provide a canister that will reduce the possibility of dust from the absorption medium entering the inhalation tube, and to provide a canister having check valves that can be easily removed for maintenance and sterilization.

SUMMARY OF THE INVENTION

In accordance with the foregoing objects, the present invention provides a unique carbon dioxide absorption canister including a container and a lid therefor for use in conjunction with closed circuit analgesic and anesthetic equipment. In the preferred embodiment, the container has a cylindrically-shaped side wall and an integral, circular bottom wall while the lid is removable and has a generally circular configuration. Means are provided for securing the lid to the container and for providing a fluid-tight seal between the lid and the upper edge portion of the cylindrical side wall. Preferably, both the container and the lid are composed of a transparent material such as an acrylic resin. An apertured tray for supporting the absorption medium, preferably composed of the same transparent material, is constructed to slide into and fit within the container and rest adjacent the inside surface of the bottom wall. A check valve is associated with an inlet channel in the bottom of the container. A suitable fitting couples the inlet channel to the exhalation tube of the analgesia equipment. The lid carries an outlet channel provided with suitable fittings for coupling the outlet channel to the inhalation tube and to the gas supply machine of the analgesia equipment. A second check valve is associated with the outlet channel. The first check valve operates to permit flow only from the inlet channel into the interior of the absorption canister, while the second check valve permits flow only from within the canister to and through the outlet channel. Both check valves are constructed so that their operation can be visually monitored through the transparent side wall, bottom wall and lid of the canister. An expansible chamber, preferably a conventional air bag, is placed in fluid communication with the interior of the cannister via a suitable fitting on the bottom wall of the container. Thus, as a patient breathes, exhaled air travels through the exhalation tube from the mask, through the inlet channel, and on through the inlet check valve to the cavity within the canister. The pressure distribution in the equipment is such that the outlet check valve will not allow flow during the exhalation cycle, causing the air bag to expand. As the patient inhales, the pressure distribution within the equipment is such that gas will flow from the cavity through the outlet valve, while the inlet valve prohibits flow, causing air within the air bag and the cavity to travel upwardly through the absorption medium on the support tray and through the outlet check valve and into the inhalation tube. Because the canister is composed of a transparent material, the operation of the check valves can be constantly visually monitored by the doctor and his assistants. Moreover, the condition of the absorption medium, normally treated with an indicator so that it turns color when it becomes saturated with carbon dioxide, can also be constantly visually monitored. Not only will the absorption medium change color from the bottom up, which change can be seen through the side wall of the canister so that it can be replaced when nearly all of the medium is exhausted, but also a flow path of least resistance causing a portion of the top layer of medium to nonuniformly turn color can be noticed through the transparent top of the canister. Another advantage of the invention is that the check valves are mounted in the canister so that they can easily be removed for cleaning, sterilization and replacement. In addition to the foregoing advantages, a simple adjustable pressure relief valve can be coupled by a suitable fitting in fluid communication with the interior of the canister through the bottom wall of the container. The relief valve, because of its location on the bottom of the container, can perform the dual functions of pressure relief and as a drain valve for draining accumulated moisture from the cannister. Additional advantages of the invention will become apparent after reading the following specification.

BRIEF DESCRIPTION OF THE DRAWINGS

A better understanding of the present invention can be derived by reading the ensuing specification in conjunction with the accompanying drawings wherein.

DESCRIPTION OF PREFERRED EMBODIMENTS

Figure 1:
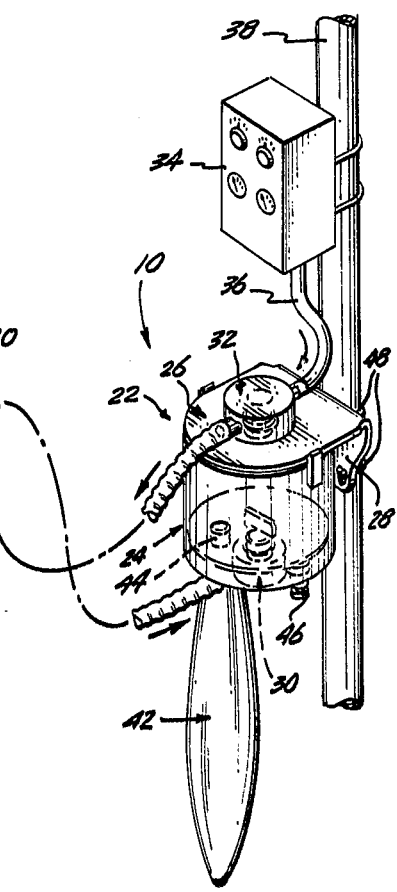
FIG. 1 is an isometric view of an analgesic administering apparatus employing the absorption canister of the present invention.

Referring first to FIG. 1, an analgesic administration apparatus, generally designated 10, includes a patient nose mask 12 having an inlet 14 and an outlet 16. An inhalation conduit 18 is connected to the inlet 14 of the nose mask 12 and an exhalation conduit 20 is connected to the outlet 16 on the nose mask 12. The absorption canister, generally designated 22, includes a container 24, and a lid 26 having an integral mounting bracket 28. The exhalation conduit 20 is connected to canister inlet 30 on the bottom of the container 24 via a suitable fitting. The inhalation conduit 18 is connected to the canister outlet in the lid 26 via a suitable fitting. A gas supply machine 34 of conventional manufacture supplies, an anesthetic gas and oxygen through a conduit 36 also coupled to canister the outlet 32 via a suitable fitting. Both the gas supply machine 34 and the canister 22 are mounted by conventional means such as U-bolts to mounting post 38 conventionally fixed to a mobile floor stand. An expansible chamber, preferably a conventional rubber air bag 42, is coupled to an expansion chamber fitting 44 located on the bottom of the container 24 which is in turn in fluid communication with the interior of the canister 22. A pressure relief valve 46 is also suitably coupled to the bottom of the container 24.

In operation, the nose mask 12 is positioned over the nose and mouth of a patient to whom analgesia is to be administered. The gas supply machine 34 is adjusted to supply gas at a flow rate normally on the order of 1 liter per minute of oxygen and 1 liter per minute of anesthetic gas, such as nitrous oxide ($N_2O$). The gas from the gas supply machine flows through the fitting adjacent the outlet 32 on the canister and through the inhalation tube 18 into the nose mask 12 and upon inhalation into the patient. Upon exhalation, gas then flows through the exhalation conduit 20 and into the canister 22. Should excessive pressure build up within the closed circuit, the pressure relief valve 46 vents excess gas to the atmosphere. When the patient exhales, the exhaled air, including carbon dioxide produced by the patient's metabolism, flows through the exhalation conduit 20 into the canister 22 through the inlet 30. As will be described later, a check valve is incorporated into the inlet in the bottom of the container 24 that only allows flow into the canister when the patient exhales. The increased volume of air created by the patient's exhalation fills the air bag 42 coupled to the bottom of the canister 22. As the patient inhales, a make-up supply of gas from the gas supply machine 34 flows through the inhalation conduit into the nose mask 12. As will also be described below, a second check valve incorporated into the outlet 32 of the canister permits flow from the canister when a patient inhales, while reverse flow through the inlet is prohibited by the first mentioned check valve. As the patient inhales, additional gas is drawn from the canister causing the air bag to partially collapse, completing the closed breathing circuit through the canister. In order to provide an effective closed circuit device, a means for absorbing the carbon dioxide produced by the patient must be employed, thus, the reason for the absorption canister. Conventionally, the absorption canister is substantially filled with an absorption medium for example, soda lime, a mixture of calcium hydroxide and potassium or sodium hydroxide. When the patient inhales, the volume of air in the closed circuit system is reduced, causing the gas from the air bag 42 to flow through the absorption medium within the canister. As it does so, carbon dioxide in the gas is absorbed upon contact by the medium, leaving relatively carbon dioxide free gas flowing through the canister outlet and to the mask.

Figure 3:
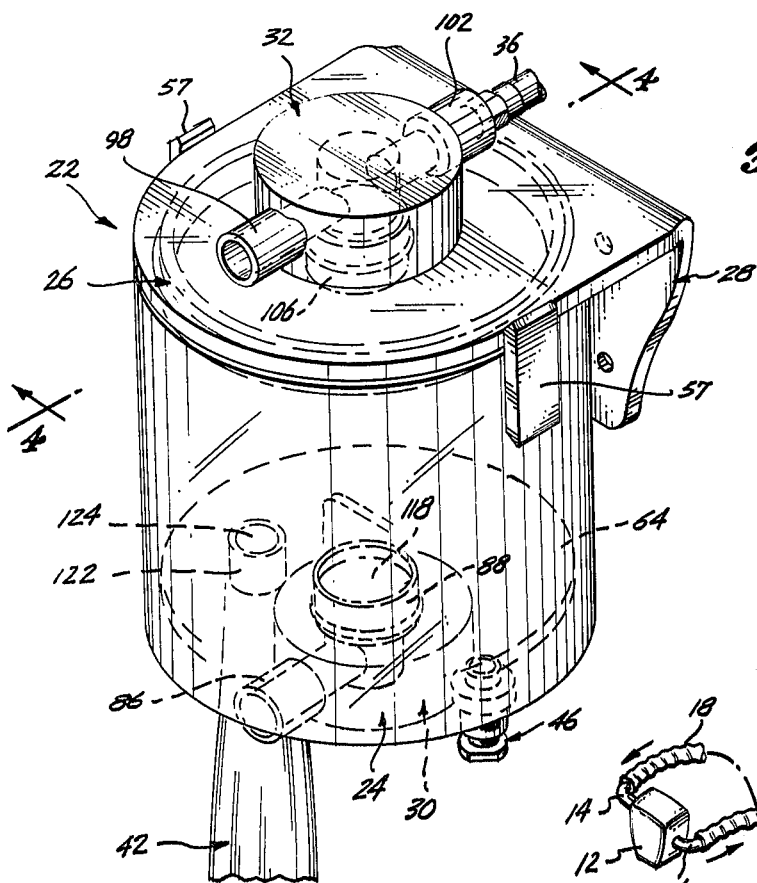
FIG. 3 is an isometric view of an assembled absorption canister of the present invention showing the visibility of the check valves mounted within the container.
Figure 4:
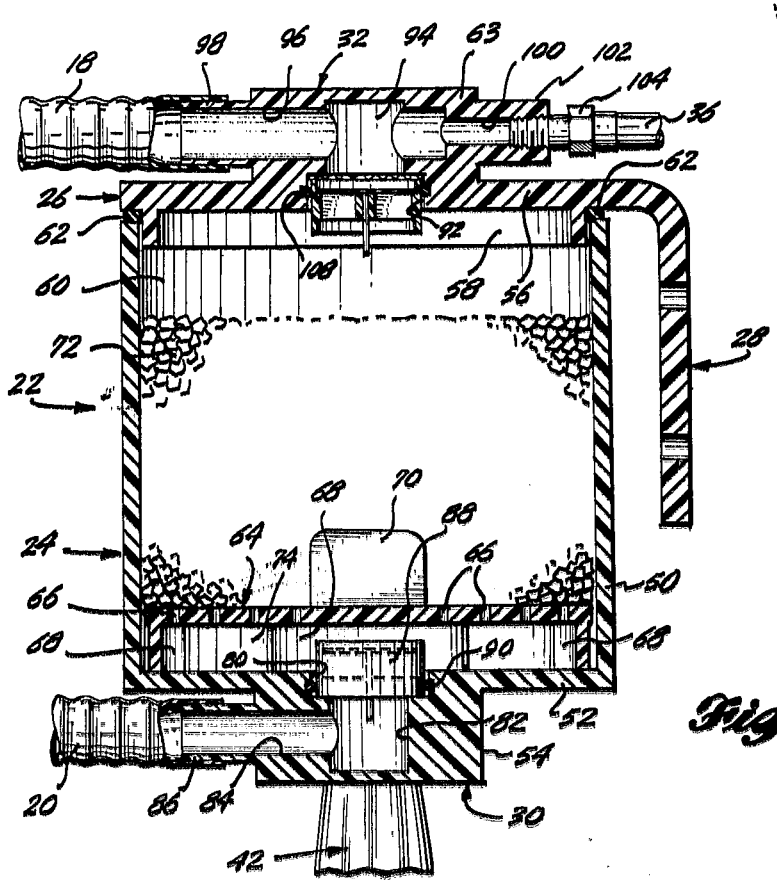
FIG. 4 is a cross-sectional view of the absorption canister of the present invention taken along section line 4—4 of FIG. 3.
Figure 2:
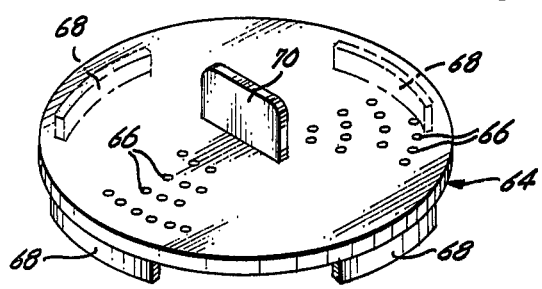
FIG. 2 is an enlarged, exploded, and partially cut away, isometric view of the absorption canister of the present invention.
Figure 6:
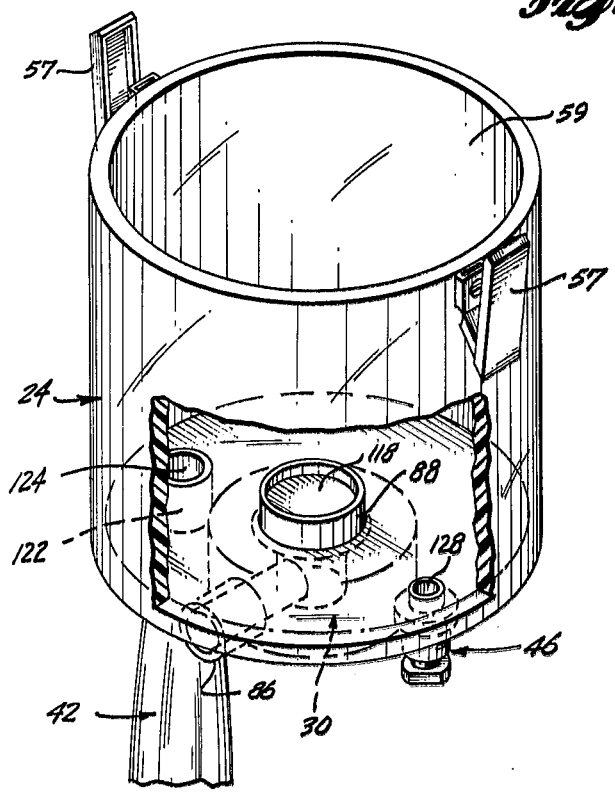
FIG. 6 is an enlarged, longitudinal sectional view of the preferred dual function relief and drain valve employed with the present invention.
Figure 6:
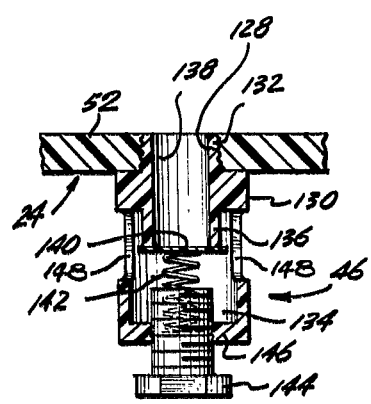

Referring now to FIGS. 2, 3 and 4, the container 24 of the absorption canister 22 has a side wall 50 in the shape of a vertically oriented, right cylindrical shell. The bottom wall 52 of the container 24 is integral with the side wall 50 and is in the shape of a circular disk having an integral, central cylindrical protrusion 54 that extends downwardly from the bottom surface of the bottom wall 52. The bottom wall 52 is oriented perpendicularly to the axis of revolution of the side wall 50. The lid 26 comprises a plate 56 that covers the open top 59 of the container 24. An annular flange 58, extending downwardly from the bottom surface of the lid 26, has an outside diameter slightly less than the inside diameter of the side wall 50 of the container. When the lid 26 is in position, the annular flange 58 extends a slight distance downwardly into the interior cavity defined within the container 24 and centers the lid over the open top 59 of the container. An O-ring 62 is interposed between the upper edge portion of the side wall 50 and the shoulder formed between the periphery of the annular flange 58 and the bottom surface of the plate 56 adjacent the periphery of the lid 26. The O-ring 62 forms a fluid-tight seal between the lid 26 and the side wall 50 of the container 24. A mounting flange or bracket 28 is formed integrally with the lid 26 and extends sidewardly from plate portion 56 of the lid to a location beyond the outside surface of the side wall 50, and thereafter extends downwardly spaced from and alongside the side wall 50 of the container 24. Suitable holes are provided in the flange 28 for insertion of suitable mounting bolts such as U-bolts 48 (shown in FIG. 1). The lid 26 has an integral, central cylindrical protrusion 63 extending upwardly from the upper surface of the plate portion 56. The lid 26 is removably secured to the container 24 by conventional draw catches 57 commercially available from Southco Inc., Lester, Pennsylvania 19113.

An absorption medium support tray 64 in the shape of a circular disk has apertures 56 extending from the botton surface to the top surface thereof. The support tray 64 is preferably oriented perpendicularly to the axis of revolution of the cylindrical shell forming the side wall 50. The support plate 64 is supported at a predetermined distance above the bottom, inside surface of the bottom wall 52 of the container 24 by four arcuate legs 68 equidistantly spaced around the plate adjacent its periphery and extending downwardly from the bottom surface thereof. The curvature of the arcuate legs 68 conform substantially to the curvature of the periphery of the support tray 64. The space below the support tray 64 and above the inside surface of the bottom wall 52 of the container forms a chamber 74, the purpose for which will become apparent later. A tray handle 70, comprising a flat relatively thin member, extends upwardly from the central portion of the support tray 64. The tray handle 70 serves as a means for grasping the support tray 64 to remove the tray from and insert it in the cavity 60 defined within the canister 22. An absorption medium 72 in the form of granules rests on top of the support tray 64 and substantially fills the cavity 60 up to a location spaced slightly below the bottom edge portion of the annular flange 58. The perferated tray acts as a diffuser to distribute the gas flowing from the chamber evenly through the absorption medium.

Fluid couplings are provided respectively between the inlet 30 and the exhalation conduit 20 and between the outlet 32 and the inhalation conduit 18 and the gas supply conduit 36. In the preferred embodiment, a cylindrical well 80 is formed in the bottom wall 52 coaxially with the axis of revolution of the container 24. The well 80 opens into the cavity 60 flush with the inside surface of the bottom wall 52 and extends downwardly therefrom into the protrusion 54. A concentric bore 82, having a diameter less than that of the well 80, extends downwardly from the well 80 and terminates short of the bottom of the protrusion 54. A second bore 84 radially oriented relative to the bore 82 communicates with the bore 82 and extends outwardly through the side of the protrusion 54. A tube 86 affixed to the protrusion 54 and having an inside diameter equal to that of bore 84 is aligned with the bore 84 to provide a coupling location for the exhalation conduit 20. In practice, the exhalation conduit 20 can be slipped over the outer surface of the tube 86 and, if desired or if necessary, can be clamped to the tube 86 with a conventional clamp (not shown).

A check valve 88 having an annular body with an outside diameter slightly less than the diameter of the well 80, but slightly greater than the diameter of the coaxial bore 82, is positioned within the well 80. The bottom of the valve body rests on the shoulder formed by the bottom surface of the well 80 between the coaxial bore 82 and the side of the well 80. An O-ring 90 is positioned in an annular recess extending radially outwardly from the side of the well 80 midway between the bottom of the well 80 and the inside surface of the bottom wall 52 of the container 24. THe O-ring is sufficiently large to form a fluid tight seal between the side of the well 80 and the outer surface of the check valve body.

A second cylindrical well 92 is formed in the lid 26 coaxially with the axis of revolution of the container 24. The well 92 opens into the cavity 60 flush with the inside surface of the lid 26. A concentric bore 94 having a diameter less than that of the well 92, extends upwardly from the well 92 and terminates short of the top of the protrusion 63. A bore 96 radially oriented relative to the bore 94 communicates with the first bore 94 and extends outwardly through the side of the protrusion 63. A tube 98 affixed to the side of the protrusion 63 and having an inside diameter equal to that of bore 96 is aligned with bore 96 to provide a coupling location for the inhalation conduit 18. In practice, the inhalation conduit 18 can be slipped over the outer surface of the tube 98 and if desired or if necessary, can be clamped to the tube 98 with a conventional clamp (not shown). The radially oriented bore 96 also extends across the first bore 94 and extends radially outwardly in a direction diametric to the location of coupling tube 98. A third smaller bore 100, concentric with the bore 96, extends outwardly from the termination of bore 96 and through another cylindrical projection 102 integral with and extending radially outwardly from the side of protrusion 63. The bore 100 opens outwardly through the end of the radial projection 102. Adjacent its outer opening, bore 102 is internally threaded to receive a threaded fitting 104 coupled to the end of the gas supply conduit 36. Gas is thus supplied to the inhalation conduit 18 through the outlet, generally designated 32, in the mmaner just described.

A second check valve 106 having an annular body with an outside diameter slightly less than the diameter of well 92, but slightly greater than the diameter of coaxial bore 94, is positioned within the well 92. The top of the valve body rests on the shoulder formed by the top surface of the well 92 between the coaxial bore 94 and the side of the well 92. On O-ring 108 is positioned in an annular recess extending outwardly from the side of the well 92 midway between the top of the well and the inside surface of the lid 26. The O-ring 108 is sufficiently large to form a fluid-tight seal between the side of the well 92 and outer surface of the valve body.

The mounting and seating arrangement for both check valves 88 and 106 allows lack of them to be removed easily for maintenance, cleaning, sterilization and replacement. In addition, if desired, flow through the canister can be easily reversed by removing the valves from their respective wells and reinserting them in reversed positions.

Figure 5:
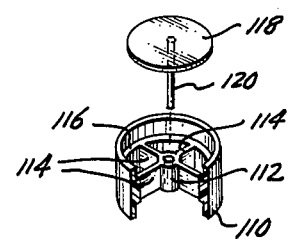
FIG. 5 is an exploded isometric view of a preferred check valve for use with the present invention.

The check valves 88 and 106 are of identical construction and are illustrated in FIG. 5. The valve has an annular body 110 with a small tube 112 positioned concentrically within the annular body. Four equidistantly spaced, radially extending arms 114 interconnect the tube 112 to the interior of the valve body 110. An upwardly facing shoulder 116 is formed on the upper, interior portion of the valve body 110 at the same level as the upper edge of the arms 114. The valve disc 118 comprises a resilient diaphragm having a centrally positioned, integral, downwardly extending stem 120 oriented perpendicularly to the plane of the diaphragm. The diaphragm is circular and has a diameter slightly less than the outside diameter of the shoulder 116. The stem 120 is sized to provide an interference fit in the bore in the tube 112. When the stem is inserted in the tube bore, the bottom surface of the diaphragm 118 in its relaxed state contacts the upper edge of the arms 114 and the top surface of the shoulder 116. When the differential pressure on the valve is greater the top of the valve, no fluid can flow through the valve. However, when the pressure differential is reversed and is greater on the bottom of the valve, the diaphragm will flex, allowing fluid to flow through the space between the interior of the annular body 110 and the outer surface of the tube 112. Check valves of this type are commercially available from U.S. Divers Corporation.

Both check valves 88 and 106 are positioned with the top of the valve oriented upwardly. In this manner, fluid can flow from the exhalation conduit 20 through the inlet 30, through the inlet check valve 88 and into the chamber 74 below the medium support tray 64. Since the pressure during exhalation will be greater on the downstream side of outlet 32 than in the cavity 60, the outlet check valve 106 will remain seated and will not allow any gas to escape from the cavity 60 into the inhalation conduit 18. Likewise, during inhalation, the pressure in the cavity 60 will be greater than the pressure in the exhalation conduit causing the inlet valve 88 to seat and thereby not allowing flow from the cavity into the outlet 30, but at the same time, outlet check valve 106 will unseat allowing flow from the cavity into the inhalation conduit 18. The orientation of the valves in conjunction with the transparent container and lid also provides an easy means for observing correct installation of the valves to prevent flow reversal through the canister or to prevent the occurrence of opposite installation of the valves, which would result in no flow through the canister.

The air bag 42 is connected to a fitting 122 affixed to the bottom of the container 24. The fitting 122 comprises a tube that extends downwardly from the outside surface of the bottom wall 52 of the container 24. A bore 124 through the bottom wall 52 communicates with the interior of the fitting 122 thus placing the air bag 42 in fluid communication with the chamber 74 below the medium support tray 64. During exhalation the volume of gas in the closed circuit will necessarily increase due to the volume of air exhausted from the patient's lungs and due to the additional make-up oxygen and nitrous oxide entering the closed circuit through the gas supply conduit 36. When this occurs, air flowing into the cavity during exhalation will first enter the chamber 74 below the medium support tray and essentially flow into the air bag 42 causing it to expand. During inhalation, the volume of air in the closed circuit system will be reduced, thus allowing air to be exhausted from the air bag 42 and allowing it to collapse. The air drawn from the air bag 42 will travel upwardly through the apertures 66 in the medium support tray 64 and flow upwardly through the absorption medium 72 in the cavity 60. As the air contacts the absorption medium, the carbon dioxide from the air will be absorbed.

In practice, the preferred absorption medium, granular soda lime, is treated with an indicator which combines with carbon dioxide to tint the soda lime blue when it is saturated with carbon dioxide, thereby providing a visual indication of when the medium is ready for replacement. A typical indicator is ethyl violet. Soda lime treated with such an indicator is available under the trademark "Sodasorb" from Dewey and Almy Chemical Division, W. R. Grace and Co., Cambridge, Mass. 02140. When this type of absorption medium is used, the advantage of positioning the inlet to the canister at the bottom of the container in conjunction with the transparent material from which the container and lid are manufactured is apparent, namely that the condition of the absorption medium can be constantly visually monitored to determine whether or not it is saturated with carbon dioxide and thus no longer doing an effective absorption job. For example, the air flowing through the medium will tend to take the path of least resistance because of the arrangement of the medium granules. Absorption of carbon dioxide along this path of least resistance will cause saturation of the medium in an isolated region much smaller in cross section that the cross-sectional area of the container 24. The gas will continue to pass through this path and result in a less than adequate amount of carbon dioxide being absorbed. When this occurs, an undesirable carbon dioxide buildup within the system will result. However, with the transparent lid and container of the present invention used in conjunction with an absorption medium that has a color indicator to indicate saturation, paths of least resistance can easily be detected by noting a small colored region on the top layer of granules of the medium. When this occurs, the canister can be vibrated slightly to readjust the absorption medium granules or the granules can be replaced as desired, In addition, the near exhaustion of the entire quantity of medium can be observed as the colored indicator in the medium will first indicate saturation adjacent the support tray and as more of the medium is saturated, the color will move upwardly in the medium. When almost all of the medium is colored, except a small layer adjacent the top of the medium, the device can be disassembled and the medium replaced.

During the respriation process, moisture is generated in the body and is exhausted along with the exhaled air. This moisture tends to condense inside the absorption canister 22. Because of the construction of the canister of the present invention, this moisture can easily be seen and is automatically removed through the pressure relief valve 46 when it opens to relieve gas pressure. The pressure relief valve is threadably inserted into an internally threaded bore 128 in the bottom wall 52 of the container 24. In the preferred embodiment, the bore 128 is situated between the protrusion 54 on the bottom wall and the periphery of the container 24. The bore 128 opens onto the inside surface of the bottom wall flush with that surface. Moisture condensing within the canister will tend to drain onto the bottom wall and is automatically removed by tilting the canister slightly so that the bore 128 resides at the lowest level, so that the moisture will run toward the bore 128. Any residual moisture can be drained from the canister by manually opening the pressure relief valve 46. Referring to FIG. 5, an enlarged cross-sectional view of the preferred relief valve 46, commercially available from Dupaco Incorporated, San Marcos, California under the name exhalation air vent valve and under part number 74970, comprises a cylindrical body 130 having a smaller diameter externally threaded tube 132 positioned coaxially with the body and extending upwardly therefrom. The tube 132 threadably engages the internal threads in the bore 128 in the bottom wall 52 of the container 24. A cylindrical cavity 134 is formed in the interior of the pressure relief valve 46. An annular flange 136 extends downwardly into the cavity 134 and has its circular opening coaxially aligned with the bore 138 of the tube 132. A thin disk 140 contacts the bottom edge of the flange 136 to cover the opening to the annular flange 136. The disc is biased against the bottom edge of the flange 136 by a coil spring 142 in compression. The coil spring is adjustably biased by interposition between the disc and a thumb screw 44 threadably inserted through a suitable, internally threaded bore in the bottom wall 146 of the valve body 130. By turning the thumb screw 144 in a clockwise direction, the spring tension is increased thereby increasing the force with which disk 140 bears against the shoulder 136. In this manner, a higher internal pressure within the cavity must be reached before the spring force is overcome. When the necessary pressure is reached, the disk 140 will unseat from the flange 136 and will exhaust into the cylindrical cavity 134 and out through apertures 148 provided in the side walls of the relief valve body 130. In a reverse manner, the relief pressure can be reduced by turning the thumb screw 144 in a counterclockwise direction to reduce the biasing force with which the spring 142 bears upon the disk 140.

Figure 7:
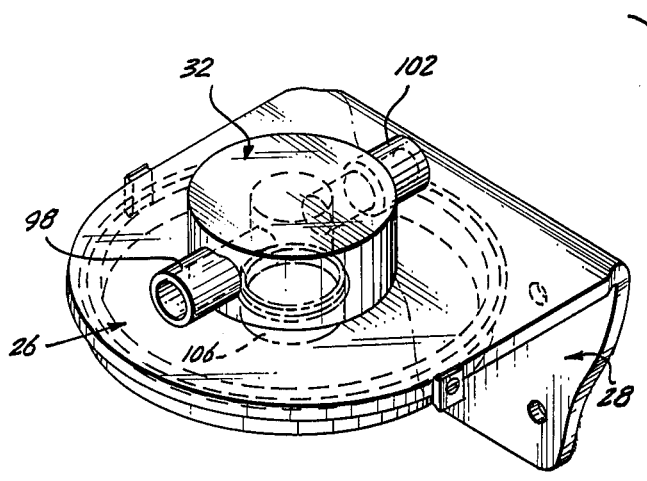
FIG. 7 is a cross-sectional view of an auxiliary coupling for the relief and drain valve for venting relieved gas to a location removed from the anesthetic administration area.
Figure 7:
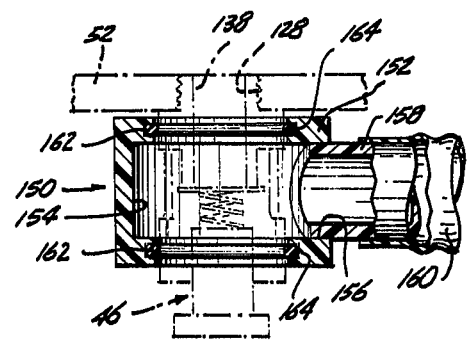

An additional advantage of the present invention is that this relief valve can be fitted with a very simple coupling to which an exhaust conduit can be attached. This conduit can be routed to a location outside the area where the doctor and his assistants are using the absorption canister of the present invention, and is preferably routed to the atmosphere outside the building in which the doctor and his assistants are working. Referring to FIG. 7, the auxiliary fitting generally designated 150 comprises an annular body 152. The annular body 152 contains an annular groove 154 extending outwardly from the inner surface of the annular body 152 at a location between the top and bottom of the body. A bore 156 extends radially outwardly through the wall of the body 152 from the annular groove 154. A tube 158 having an outer diameter equal to that of the inner diameter of the bore 156 is interference fitting into the bore and serves as a coupling location for the exhaust conduit 160, here shown to be a conventional corrugated tube. Smaller outwardly extending annular grooves 162 are located on the inside surface of the body on each side of the large annular groove 154. O-rings 164 are fitted into each of the annular grooves. In use, the fitting 150 is first positioned below the relief valve 46 and then slipped upwardly over the relief valve body 130. The inside diameter of the annular body 152 is slightly larger than the outside diameter of the pressure relief valve body 130 so that the upper O-ring 164 will seat against the outside upper surface of the valve body 130 and the lower O-ring 164 will seat against the lower outside surface of the valve body, thus providing a fluid-tight chamber around the relief apertures in the valve body. Should the pressure within the cavity 60 in the canister exceed the pressure preset with the thumb screw 144, gas exhausting from the relieve valve will be captured by fitting 150 and exhausted to a safe location through the exhaust conduit 160.

Another of the principal advantages of the present invention lies with the particular check valves used in conjunction with the transparent, resinous material from which the container 24 and the lid 26 are manufactured. As can be seen in FIG. 3, the valve disk 118 of the inlet check valve 88 is readily visible through the side wall 50 of the container 24. Although the line of sight to the valve shown in FIG. 3 would be obscured when the absorption medium is in place, a similar line of sight through the side wall 50 into the cavity 74 below the medium support tray 64 will allow observation of the valve when the medium is in place. Thus, the operation of the valve can be visually monitored throughout use of the canister. During exhalation, the valve disk 118 will flex sufficiently to rise above the upper edge of the body of the inlet check valve 88. Thus, the doctor or his assistant administering analgesia can assure himself that the inlet check valve 88 is always functioning properly. Likewise, the operation of the outlet check valve 88 can be observed by viewing downwardly through the upward projection on the lid 26. The disk 118 of the outlet check valve can thus be observed and the operation of the check valve visually monitored.

Although the absorption canister of the present invention has been described in relation to its use with analgesia equipment, it is to be understood that the invention can also be used with equipment for administering an anesthetic, although the composition of the O-ring seals and other components might have to be changed to prevent degradative attack by certain anesthetic gases. When the term "anesthesia" and derivatives thereof are used herein, they are intended to encompass both anesthesia and analgesia and their derivatives. One of ordinary skill in the art will be able to effect various changes, alterations and substitutions of equivalents without departing from the original intent and scope of the invention as disclosed. For example, any of a variety of check valves can be employed with the present invention as long as their operation can be visually observed through the transparent walls, bottom and lid of the canister. Moreover, a variety of pressure relief valves can be employed as desired. In addition, the shape of the container 24 is not critical and could be, if desired, manufactured in square or rectangular cross section rather than the preferred circular cross section described above. Moreover, if desired, the air bag fitting can be positioned at any convenient location on the canister including the lid. It is required, however, that the air bag be in communication with the interior cavity of the canister at a location in the fluid path between the inlet and outlet check valves. It is therefore intended that the grant of Letters Patent on the present invention be limited only by the definition contained in the appended claims.

What is claimed is:

1. In an apparatus for administering a gaseous anesthetic to a patient including a gas supply machine for metering selected amounts of anesthetic gas, a mask for supplying said gas to a patient, said mask having an inlet and an outlet, an inhalation conduit coupled to the inlet of said mask and operatively coupled to receive gas from said gas machine, and an exhalation conduit coupled to the outlet of said mask, an improved carbon dioxide absorption canister operatively coupled to said inhalation and exhalation conduits comprising:

a container having a side wall, a bottom wall, and an open top, said side wall and said bottom wall defining a cavity therein for holding medium to absorb carbon dioxide from gas present within said cavity, said side wall and said bottom wall of said container being composed of a transparent, resinous material, said bottom wall having a well therein extending downwardly from the inside surface of said bottom wall outwardly toward the outside surface of said bottom wall and terminating short thereof, said bottom wall further including a bore communicating between said well and the exterior of said bottom wall, a first check valve having an annular body positioned in said well and extending upwardly from the inside surface of said bottom wall, said first check valve including means for admitting gas into said cavity through said bore and for preventing gas from escaping from said bore, said check valve being constructed so that the operation thereof can be visually monitored through the walls of said container,
first fitting means associated with the bore on the bottom of the container for operatively coupling said exhalation conduit to the bore on the bottom of said container,
a lid for covering the open top of said container, said lid having an outlet therein,
means for securing said lid to said container,
means associated with said lid and said container for forming a fluid-tight seal therebetween when said lid is covering the open top of said container,
a second check valve positioned in the outlet in said lid, said second check valve including means for allowing gas to escape from said cavity through said outlet and for preventing gas from entering said outlet, said container, said lid and said first and second check valves cooperating to define a unidirectional fluid path from said first fitting means, through said cavity, and to said outlet, and,
second fitting means associated with the outlet on said lid for operatively coupling said outlet to said inhalation conduit and to said gas machine.

2. The improvement of claim 1 further comprising:
means defining an expansible chamber and coupling means associated therewith for operatively placing said chamber in fluid communication with said cavity at a location along said fluid path between the location of said first and second check valves.

3. The improvement of claim 2 wherein the bottom wall of said container has a bore therethrough, said coupling means placing said expansible chamber in fluid communication with said cavity through said bore.

4. The apparatus of claim 1 wherein said lid has an inside surface and an outside surface and wherein said lid is composed of a transparent resinous material, said lid further having a well therein extending outwardly from the inside surface thereof and terminating short of the outside surface thereof, said second check valve having an annular body and being sized to fit into the well in said lid, and means for forming a fluid seal between said second check valve and the well in said lid, said outlet in said lid including a bore communicating with said well and, said second fitting means being associated with said bore in said lid to operatively couple said outlet to said inhalation conduit and to said gas machine.

5. In an apparatus for administering a gaseous anesthetic to a patient including a gas supply machine for metering selected amounts of anesthetic gas, a mask for supplying said gas to a patient, said mask having an inlet and an outlet, an inhalation conduit coupled to the inlet of said mask and operatively coupled to said gas machine, and an exhalation conduit coupled to the outlet of said mask, an improved carbon dioxide absorption canister operatively coupled to said inhalation and exhalation conduits comprising:
a container having a side wall, a bottom wall, and an open top, said side wall and said bottom wall being composed of a transparent, resinous material and defining a cavity therein for holding a medium to absorb carbon dioxide from gas present in said cavity, said container having an inlet in the bottom wall thereof,
a first check valve positioned in the inlet in said bottom wall, said first check valve being positioned within said container, said first check valve including means for admitting gas into said cavity through said inlet and for preventing gas from escaping from said inlet, said first check valve being constructed so that operation thereof can be visibly monitored through the side wall and through the bottom wall of said container,
first fitting means associated with the inlet on the bottom wall of said container for operatively coupling said exhalation conduit to said container,
a lid for covering the open top of said container, said lid having an outlet therein,
means for securing said lid to said container,
means associated with said lid and said container for forming a fluid-tight seal therebetween when said lid is covering the open top of said container,
a second check valve positioned in the outlet in said lid, said second check valve including means for allowing gas to escape from said cavity through said outlet and for preventing gas from entering said cavity through said outlet, said container, said lid and said first and second check valves thereby defining a unidirectional fluid path from said inlet, through said cavity, and to said outlet,
second fitting means associated with the outlet in said lid for operatively coupling said outlet to said inhalation conduit and to said gas machine, and
tray means for supporting absorption medium within said cavity, said tray means being sized to fit within said cavity in sliding relation relative to the inner surface of said side wall, said tray means having legs thereon, said legs extending from said tray means so as to rest on the bottom wall of said cavity, said legs spacing said tray means above the bottom of said cavity to define an open chamber between said tray means and the bottom of said container within said cavity, said tray means having apertures therein placing said chamber in fluid communication with the portion of said cavity above said tray means.

6. The improvement of claim 5 further comprising:
an upwardly extending projection affixed to the central portion of said tray means.

7. The improvement of claim 5 wherein the side wall of said container is a cylindrical shell having a lower edge portion and an upper edge portion and wherein said bottom wall is a first circular plate integral with the lower edge portion of said shell, wherein said lid is a second circular plate carrying a downwardly extending annular shoulder thereon, said shoulder being sized to fit within said cavity and center said lid over said open top, said second circular plate being sized to cover the top of said cavity and to engage the upper edge portion of said cylindrical shell, and wherein said tray means is a third circular plate.

8. In an apparatus for administering a gaseous anesthetic to a patient including a gas supply machine for metering selected amounts of anesthetic gas, a mask for supplying said gas to a patient, said mask having an inlet and an outlet, an inhalation conduit coupled to the inlet of said mask and operatively coupled to said gas machine, and an exhalation conduit coupled to the outlet of said mask, an improved carbon dioxide absorption canister operatively coupled to said inhalation and exhalation conduits comprising:
a container having a side wall, a bottom wall, and an open top, said side wall and said bottom wall being composed of a transparent, resinous material and defining a cavity therein for holding a medium to absorb carbon dioxide from gas present in said cavity, said container having an inlet in the bottom wall thereof, said container further having a cylindrical well extending downwardly from the inside surface of said bottom wall and a bore of lesser diameter than said well communicating between said well and said inlet of said container, said well having an outwardly extending annular groove in the side thereof for receiving an O-ring, and an O-ring positioned in the annular groove in the side of the inlet of said container, a first check valve positioned within said well and having a annular body and being removable from the inside of said container, said O-ring forming a fluid-tight seal between the side of said well and the outer surface of said check valve body, said first check valve including means for admitting gas into said cavity through said inlet of said container and for preventing gas from escaping from said inlet, at least a portion of said first check valve being positioned inside said container and further being constructed so that operation thereof can be visually monitored through the side wall and through the bottom wall of said container, first fitting means associated with the inlet in said bottom wall of said container for operatively coupling said exhalation conduit to said container, a lid for covering the open top of said container, said lid having an outlet therein, said lid being composed of a transparent resinous material, said lid further having a cylindrical well extending upwardly from the inside surface thereof and a bore of lesser diameter than said well communicating with said outlet in said lid, said well in said lid having an outwardly extending annular groove in the side thereof for receiving an O-ring, and an O-ring positioned in the annular groove in the side of the outlet in said lid, means for securing said lid to said container, means associated with said lid and said container for forming a fluid-tight seal therebetween when said lid is covering the open top of said container, a second check valve having an annular body and being positioned in the well in said lid and being removable from the well in said lid in an inward direction relative to said lid, said O-ring in the groove in said lid forming a fluid-tight seal between the side of said well and the outer surface of said second check valve body, said second check valve including means for allowing gas to escape from said cavity through said outlet of said container and for preventing gas from entering said cavity through said outlet, said container, said lid and said first and second check valves thereby defining a unidirectional fluid path from said inlet of said container, through said cavity, and to said outlet of said container, at least a portion of said second check valve being positioned within said container and being constructed so that operation thereof can be visually monitored through said lid and through the side wall of said container, and second fitting means associated with the outlet in said lid for operatively coupling said outlet to said inhalation conduit and to said gas machine.

9. The improvement of claim 8 wherein the bore associated with the well in the bottom wall is coaxial with said well and extends downwardly from the bottom of said well, said well and said bore cooperating to form a shoulder spaced downwardly from the inside surface of said bottom wall, said first check valve being removably seated against said shoulder.

10. The improvement of claim 9 wherein the bore associated with the well in said lid is coaxial therewith and extends upwardly from the upper portion of the well in said lid, the well and bore in said lid cooperating to form a shoulder spaced upwardly from the inside surface of said lid, said second check valve being removably seated against said shoulder.

11. In an apparatus for administering a gaseous anesthetic to a patient including a gas supply machine for metering selected amounts of anesthetic gas, a mask for supplying said gas to a patient, said mask having an inlet and an outlet, an inhalation conduit coupled to the inlet of said mask and operatively coupled to said gas machine, and an exhalation conduit coupled to the outlet of said mask, an improved carbon dioxide absorption canister operatively coupled to said inhalation and exhalation conduits comprising:

a container having a side wall, a bottom wall, and an open top, said side wall and said bottom wall defining a cavity therein for holding an absorption medium to absorb carbon dioxide from gas present within said cavity, said container having an inlet in the bottom wall thereof, said bottom wall having an inside surface and a channel therethrough, said channel having an opening into said cavity, said opening being oriented flush with said inside surface, a first check valve and means for operatively coupling said check valve to the inlet in said bottom wall, said first check valve including means for admitting gas into said cavity through said inlet and for preventing gas from escaping from said inlet, first fitting means associated with the inlet in said bottom wall of said container for operatively coupling said exhalation conduit to said container, a lid for covering the open top of said container, said lid having an outlet therein, means for securing said lid to said container, means associated with said lid and said container for forming a fluid-tight seal therebetween when said lid is covering the open top of said container, a second check valve positioned in the outlet in said lid, said second check valve including means for allowing gas to escape from said cavity through said outlet and for preventing gas from entering said cavity through said outlet, said container, said lid and said first and second check valves thereby defining a unidirectional fluid path from said inlet of said container, through said cavity and to said outlet of said container, second fitting means associated with said outlet in said lid for operatively coupling said outlet to said inhalation conduit and to said gas machine, and a pressure actuated relief valve and means coupling said relief valve to said channel to place said relief valve in fluid communication with said cavity, said relief valve being adjustable to an open position to drain liquid that has accumulated on said inside surface from said cavity.

12. In an apparatus for administering a gaseous anesthetic to a patient including a gas supply machine for metering selected amounts of anesthetic gas, a mask for supplying said gas to a patient, said mask having an inlet and an outlet, an inhalation conduit coupled to the inlet of said mask and operatively coupled to receive gas from said gas machine, and an exhalation conduit coupled to the outlet of said mask, an improved carbon dioxide absorption canister operatively coupled to said inhalation and exhalation conduits comprising:

a container having a side wall, a bottom wall, and an open top, said side wall and said bottom wall defining a cavity therein for holding a medium to absorb carbon dioxide from gas present within said cavity, said bottom wall having an inlet therein, a first check valve positioned in the inlet in said bottom wall, said first check valve including means for passing gas through said inlet only in a first direction relative to said cavity, first fitting means associated with the inlet in said bottom wall of said container for operatively coupling said inlet to said exhalation conduit, a lid for covering the open top of said container, said lid having an inside surface and an outside surface, said lid being composed of a transparent resinous material, said lid having a well therein extending upwardly and outwardly from the inside surface thereof and terminating short of the outside surface thereof and further having a bore of lesser diameter than said well communicating between said well and said outlet, said well having an outwardly extending annular groove in the side thereof for receiving an O-ring, and an O-ring positioned in the annular groove in the side of the outlet in said lid, means for securing said lid to said container, means associated with said lid and said container for forming a fluid-tight seal therebetween when said lid is covering the open top of said container, a second check valve removably mounted in said well, said second check valve including means for passing gas through said bore in a direction opposite to said first direction relative to said cavity, said first and second check valves cooperating to provide a unidirectional gas flow path through said cavity, said second check valve having an annular body and being removable in an inward direction relative to the inside surface of said lid, said O-ring in the well in said lid forming a fluid-tight seal between the side of said well in said lid and the outer surface of the body of said second check valve, said container, said lid and said first and second check valves cooperating to define a unidirectional fluid path through said cavity, said second check valve having an annular body and being sized to fit into said well, and means for forming a fluid-tight seal between said second check valve and said well, said lid further having a bore therein communicating with said well, and second fitting means associated with said bore in said lid for operatively coupling said bore to said inhalation conduit and to said gas machine.

13. The improvement of claim 12 wherein the means of said first check valve admits gas into said cavity through the inlet in said bottom wall and prevents gas from escaping from said cavity and wherein the means of said second check valve allows gas to escape from said cavity and prevents gas from entering said cavity through said bore.

14. The improvement of claim 12 wherein the bore associated with said well is coaxial therewith and extends upwardly from the upper portion of said well, said well and said bore cooperating to form a shoulder spaced upwardly from the inside surface of said lid, said second check valve being removably seated against said shoulder.

* * * * *